US00PP27957P3

(12) United States Plant Patent
Roy et al.

(10) Patent No.: US PP27,957 P3
(45) Date of Patent: May 2, 2017

(54) HOP PLANT NAMED 'ADHA 483'

(50) Latin Name: *Humulus lupulus*
Varietal Denomination: ADHA 483

(71) Applicants: Leslie Roy, Moxee, WA (US); Gary Morford, Wapato, WA (US)

(72) Inventors: Leslie Roy, Moxee, WA (US); Gary Morford, Wapato, WA (US)

(73) Assignee: AMERICAN DWARF HOP ASSOCIATION, LLC, Moxee, WA (US)

( * ) Notice: Subject to any disclaimer, the term of this patent is extended or adjusted under 35 U.S.C. 154(b) by 0 days.

(21) Appl. No.: 14/121,496

(22) Filed: Sep. 12, 2014

(65) Prior Publication Data

US 2015/0135379 P1 May 14, 2015

Related U.S. Application Data

(60) Provisional application No. 61/960,234, filed on Sep. 13, 2013.

(51) Int. Cl.
*A01H 5/02* (2006.01)

(52) U.S. Cl.
USPC ..... Plt./236

(58) Field of Classification Search
USPC ..... Plt./236
See application file for complete search history.

(56) References Cited

U.S. PATENT DOCUMENTS

PP23,674 P2 * 6/2013 Jeske et al. ..... Plt./236

* cited by examiner

*Primary Examiner* — Susan McCormick Ewoldt
(74) *Attorney, Agent, or Firm* — Ballew Law

(57) ABSTRACT

A new hop plant named 'ADHA 483' is disclosed. The cones of 'ADHA 483' mature in mid to late September in Moxee, Wash., and yield a crop of 2200 to 2300 pounds per acre. 'ADHA 483' is used for its semi-dwarf size and aromatic quality.

4 Drawing Sheets

Genus and species: *Humulus lupulus*.
Variety denomination: 'ADHA 483'.

STATEMENT REGARDING FEDERALLY SPONSORED RESEARCH OR DEVELOPMENT

None

BACKGROUND OF THE INVENTION

'ADHA 483' is a product of a controlled breeding program carried out by the inventor in the Yakima Valley of Washington State. 'ADHA 483' was one of several seedlings resulting from cross number 04-088 made in 2004 with female parent Toyomodori (not patented) and an open pollination cross with an unknown male parent. A single plant of 'ADHA 483' was selected in 2005.

In 2008 that single plant was asexually propagated in Toppenish, Wash. by softwood cuttings into 100 plants, which were planted in the area of Toppenish, Wash. These 100 plants were observed and evaluated for several years, and in 2010 were asexually propagated by softwood cuttings into approximately 450 plants for further observation and evaluation in Moxee, Wash. In 2012, the 'ADHA 483' plants were again expanded by softwood cuttings for observation and evaluation of a large scale test plot in Moxee, Wash. Throughout several generations of asexual propagation, 'ADHA 483' has been observed to retain its distinctive characteristics and has remained true to type.

BRIEF DESCRIPTION OF THE PHOTOGRAPHS

FIG. 3 illustrates the bine of a mature 'ADHA 483' hop plant; and.

Figure 1:
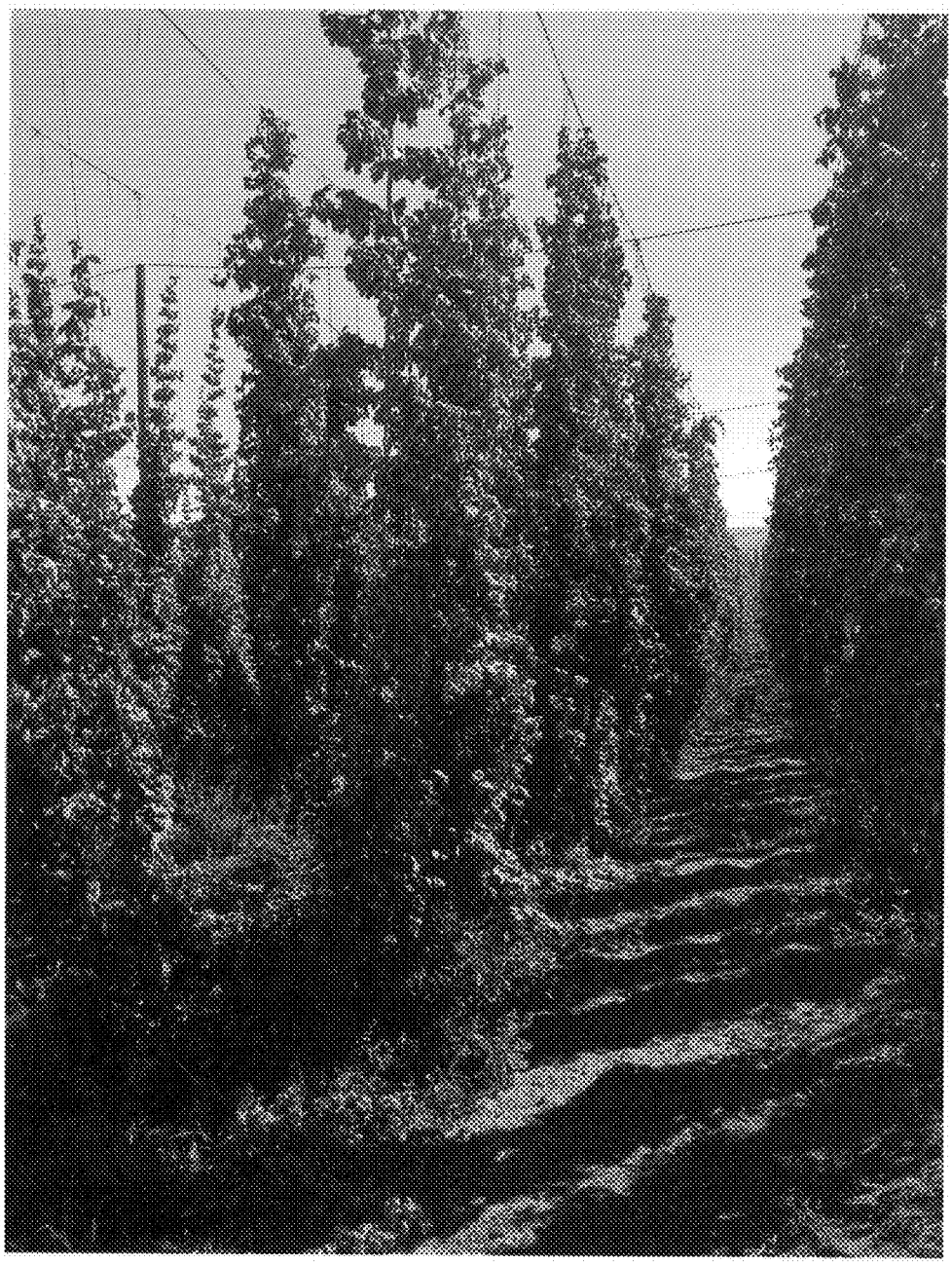
FIG. 1 illustrates a mature 'ADHA 483' hop plant grown on a trellis.
Figure 2:
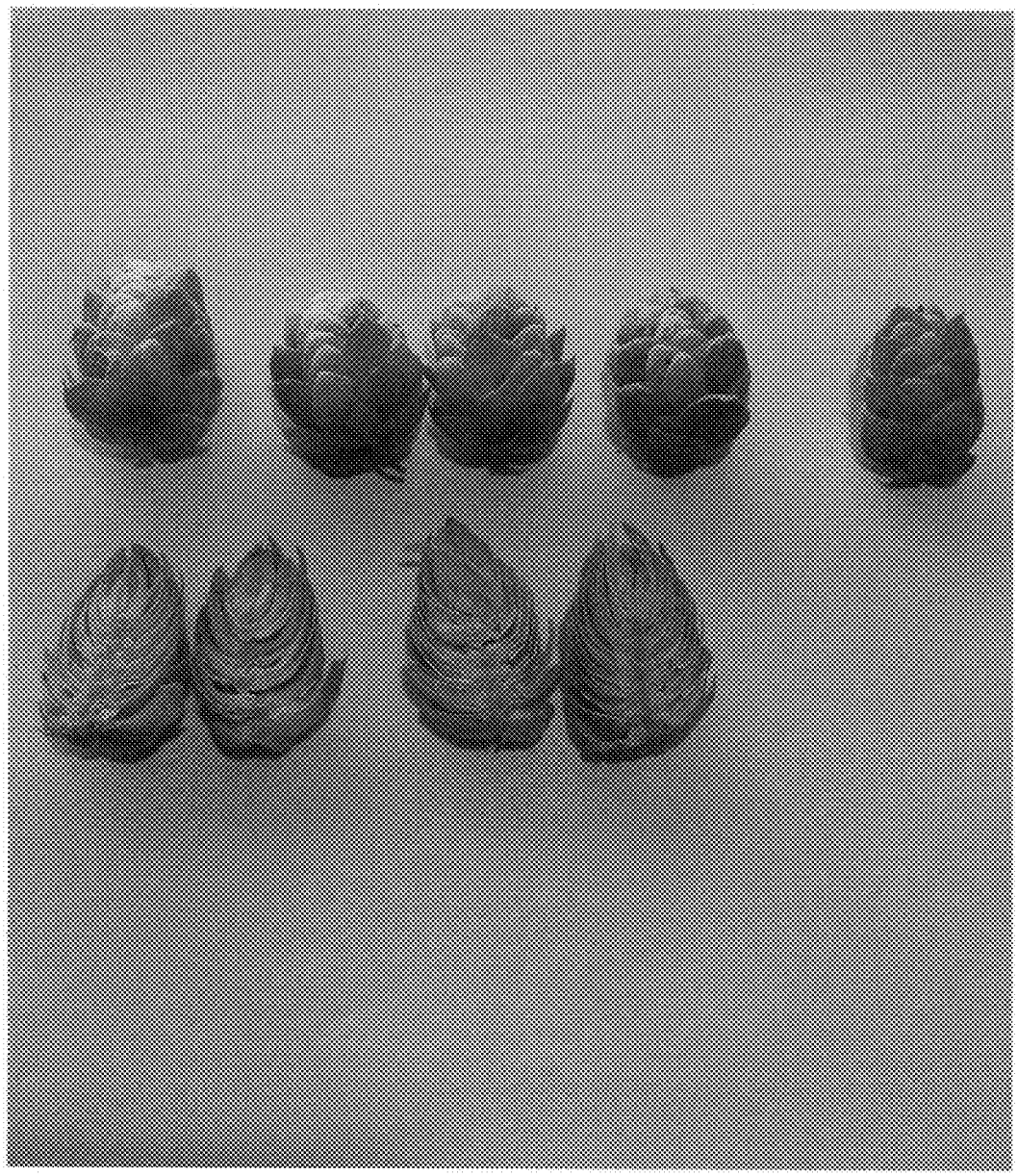
FIG. 2 illustrates whole cones and cross sections of cones of the 'ADHA 483' hop plant.
Figure 3:
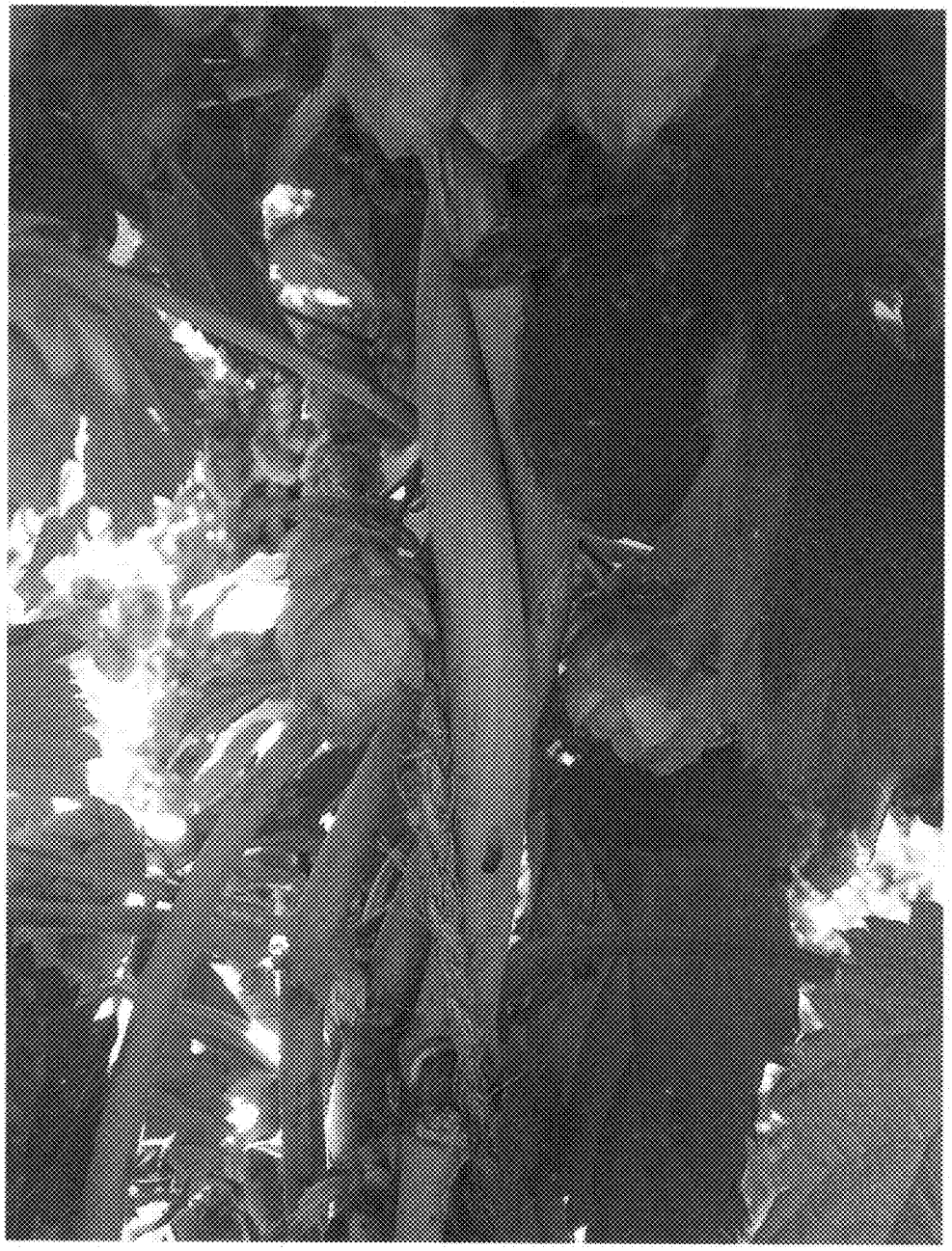
Figure 4:
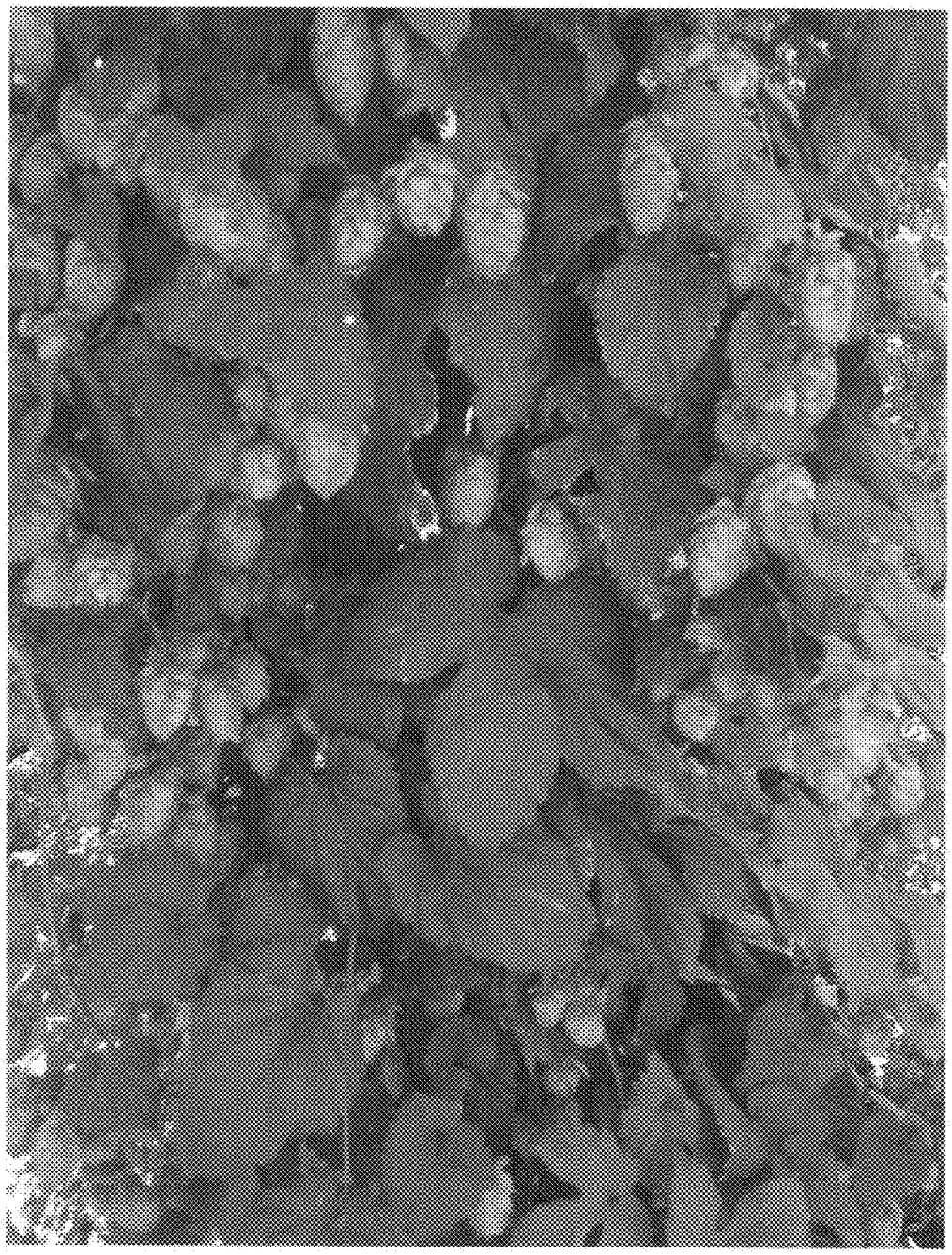
FIG. 4 illustrates the cones and leaves of a mature 'ADHA 483' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2013 growing seasons at Moxee, Wash.

'ADHA 483' is distinguishable from its parent plants ('Toyomidori' mother and unknown father). 'ADHA 483' is distinguishable from its unknown male parent because ADHA 483 is a female plant with flowers that develop into mature hop cones without producing pollen, while flowers of its unknown father male plant will always produce pollen without developing into mature hop cones.

Table 1. sets forth some of the distinguishing characteristics of 'ADHA 483' as compared to its female parent 'Toyomidori' and to the hop variety 'Summit' (U.S. Plant Pat. No. 18,039):

TABLE 1

| Characteristic | 'Toyomodori' | 'ADHA 483' | 'Summit' |
|---|---|---|---|
| Alpha Acid (α-Acids, % db) | 12.2 ± 0.6 | 14-16 | 18-19 |
| Beta Acids (β-Fraction, % db) | 7.2 ± 0.3 | 4.0-5.5 | 3.3-4.3 |
| Total Oil (ml/100 g) | 0.69 ± 0.19 | 1.6-2.5 | 1.5 |
| Myrcene (% of Total Oil) | 27 ± 5 | 46-55 | 48.5 |

It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. The color chart used was The Royal Horticultural Society Colour Chart, Copyright 2001, and all color observations were made outdoors in full sunlight.

Ploidy: Diploid.

Use: Brewing beer.

Harvest date: September 15 to 25 during the 2010-2012 growing seasons, Moxee, Wash.

Time of flowering: Considered to be early compared to other common hop varieties grown in Central Washington.

Crop yield: 2200 to 2300 pounds per acre.

Disease susceptibility: Tolerant of both downy mildew and powdery mildew.

Pest susceptibility: Average susceptibility to pests, including hop aphids and two spotted spider mites.

Plant shape: Columnar when grown on a typical hop trellis.

Bine:

*Color*.—Green Group 144B.

*Stripe*.—Green Group 143B.

*Bine diameter*.—10.25 mm at base; 13.2 mm at 6 feet; and no measurement taken at terminal end.

Leaf:

*Leaf arrangement*.—Opposite.

*Mature leaf shape*.—Palmately lobed.

*Leaf apex shape*.—Subobtuse with a dendate margin.

*Leaf base shape*.—Cordate.

*Color of mature leaf upper surface*.—Green Group 136A.

*Color of mature leaf lower surface*.—Green Group 137C.

*Number of lobes*.—3-7.

*Margin*.—Serrate.

*Serrations per inch*.—5-7.

*Average length of mature leaf*.—12 cm.

*Average width of mature leaf*.—17 cm.

*Vein color*.—Yellow Green 144B.

*Venation pattern*.—Palmate.

Petiole:

*Average petiole length (mature)*.—6.5 cm.

*Average petiole diameter*.—4 mm.

*Petiole color at base*.—Yellow Green Group 144C.

Cone:

*Cone shape*.—Orbicular-ovate.

*Cone tip shape*.—Ovate.

*Cone average length*.—2.5 cm.

*Cone average width*.—2.25 cm.

*Cone average weight*.—0.996 mg.

*Lupulin gland color*.—Ranging between Golden Yellow 2A to Yellow Green 150A (not distinctive of this variety).

*Lupulin gland shape*.—Pedunculated oblong polyps.

*Average number of lupulin glands per cone*.—65,100.

Bracts:

*Bract shape*.—Ovoid.

*Bract average length*.—1.2 cm.

*Bract average width*.—1.2 cm.

*Bract apex length*.—Short.

*Bract tip shape*.—Cuspidate.

*Bract tip position*.—Slightly flared.

*Bract tip color*.—Yellow Green Group 144A.

*Bract middle color*.—Yellow Green Group 144D.

*Bract base color*.—Yellow Green Group 145C.

*Average number of lupulin glands per bract*.—1,050.

Bracteoles:

*Bracteole color*.—Yellow Green Group 146B.

*Bracteole average length*.—1,3 cm.

*Bracteole average width*.—0.7 cm.

*Bracteole shape*.—Obtuse.

*Bracteole compactness*.—Slightly open.

Analytical characteristics:

*Alpha acid*.—14-16%.

*Beta acid*.—4.0-5.5%.

*Cohumulone*.—38-45%.

*Humulene*.—14-18% of total oils.

*Caryophyllene*.—8-12% of total oils.

*Humulene/caryophyllene ratio*.—14-18% of total oils.

*Myrcene*.—46-55% of total oils.

*Farnesene*.—<1% of total oils.

*Total oil*.—1.6-2.5 ml/100 g.

*Hop storage index (HSI)*.—The cones of the present variety experience a 24.8% transformation of alpha acids after about 6 months of storage at 22° C.

What is claimed is:

1. A new and distinct hop plant as shown and described herein.

* * * * *